US009963647B2

(12) United States Patent
Koseoglu

(10) Patent No.: US 9,963,647 B2
(45) Date of Patent: May 8, 2018

(54) METHOD TO OPTIMIZE CRUDE SLATE FOR OPTIMUM HYDRODESULFURIZATION PERFORMANCE

(71) Applicant: Saudi Arabian Oil Company, Dhahran (SA)

(72) Inventor: Omer Refa Koseoglu, Dhahran (SA)

(73) Assignee: SAUDI ARABIAN OIL COMPANY, Dhahran (SA)

(*) Notice: Subject to any disclaimer, the term of this patent is extended or adjusted under 35 U.S.C. 154(b) by 385 days.

(21) Appl. No.: 14/711,536

(22) Filed: May 13, 2015

(65) Prior Publication Data

US 2016/0334382 A1    Nov. 17, 2016

(51) Int. Cl.
| | | |
|---|---|---|
| C10G 45/72 | (2006.01) | |
| C10G 49/26 | (2006.01) | |
| G01N 33/28 | (2006.01) | |
| C10G 45/08 | (2006.01) | |
| C10G 45/02 | (2006.01) | |
| C10G 45/04 | (2006.01) | |

(Continued)

(52) U.S. Cl.
CPC .............. *C10G 45/72* (2013.01); *C10G 45/02* (2013.01); *C10G 45/04* (2013.01); *C10G 45/08* (2013.01); *C10G 49/26* (2013.01); *C10L 1/08* (2013.01); *G01N 33/225* (2013.01); *G01N 33/2835* (2013.01); *C10L 2270/026* (2013.01)

(58) Field of Classification Search
CPC ........ C10G 45/08; C10G 45/72; C10G 49/26; G01N 33/2835; G01N 33/287
See application file for complete search history.

(56) References Cited

U.S. PATENT DOCUMENTS 5,841,678 A * 11/1998 Hasenberg ............. C10G 45/72
700/29
6,063,265 A   5/2000 Chiyoda et al.
7,959,795 B2  6/2011 Ho et al.
(Continued)

FOREIGN PATENT DOCUMENTS

EP         2 497 816         9/2012

OTHER PUBLICATIONS

Erick Yair Miranda-Galindo et al: "Multiobjective Optimization of a Hydrodesulfurization Process of Diesel Using Distillation with Side Reactor", Industrial & Engineering Chemistry Research, vol. 53, No. 42. Oct. 22, 2014 (Oct. 22, 2014). pp. 16425-16435, XP055294183, US, ISSN: 0888-5885, DOI: 10.1021/ie501940v.

*Primary Examiner* — Renee Robinson
(74) *Attorney, Agent, or Firm* — Leason Ellis LLP

(57) ABSTRACT

Methods are provided for selecting optimal operating conditions for the hydrodesulfurization of a liquid hydrocarbon feed in a reactor. According to one aspect, a desired sulfur content of the product stream is selected. The carbazoles content of a first liquid hydrocarbon feed is measured, and a reaction order for the first liquid hydrocarbon feed is calculated based on the measured carbazoles content. An operating severity index based on the calculated reaction order is then calculated. According to one aspect, the operating severity index comprises an operating temperature of the reactor to yield the product stream with the desired sulfur content from the first liquid hydrocarbon feed. According to another aspect, the carbazoles content of a plurality of liquid hydrocarbon feeds are measured to generate a database of the measured carbazoles content.

21 Claims, 3 Drawing Sheets

Figure 1:
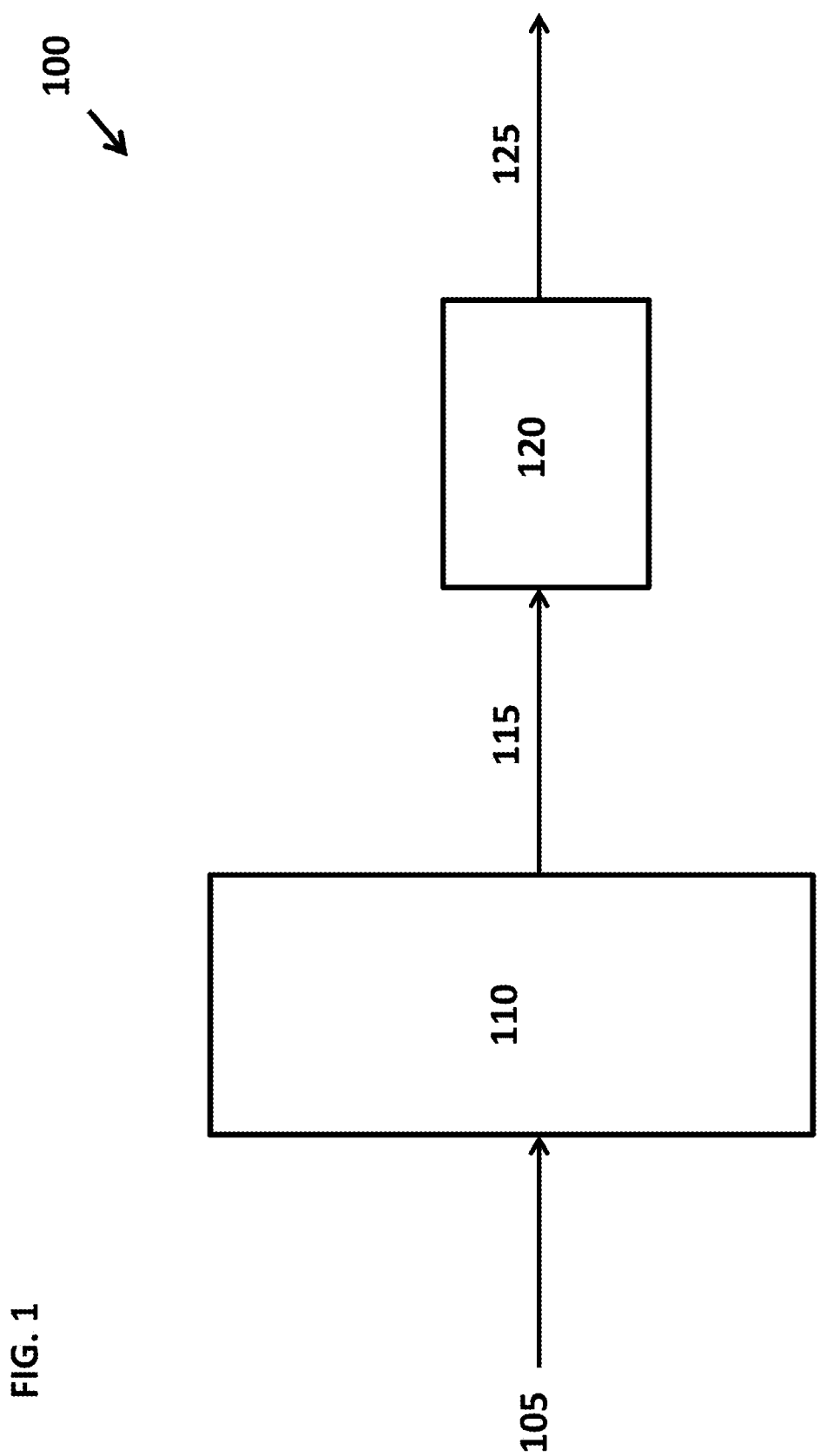

(51) Int. Cl.
    *C10L 1/08*     (2006.01)
    *G01N 33/22*    (2006.01)

(56) References Cited

U.S. PATENT DOCUMENTS

| | | |
|---|---|---|
| 8,444,850 B2 | 5/2013 | Ho et al. |
| 8,930,149 B1 | 1/2015 | Koseoglu |
| 2006/0249429 A1 | 11/2006 | Iki et al. |
| 2011/0036755 A1 | 2/2011 | Ho et al. |

* cited by examiner

METHOD TO OPTIMIZE CRUDE SLATE FOR OPTIMUM HYDRODESULFURIZATION PERFORMANCE

TECHNICAL FIELD

The present application relates to an improved method for optimizing crude oil slate at a refinery or the like and/or selecting optimal operating conditions for a process performed at the refinery.

BACKGROUND

Crude oil is an abundant energy source found throughout the world and exists in many different forms. In fact, there are over 200 different crude oils traded worldwide. In general, crude oils are complex mixtures of thousands of hydrocarbons, such as paraffins and aromatic hydrocarbons, which can be classified by their density (e.g., API gravity). For example, "light" crude oil has a low density and "heavy" crude oil has a high density.

While there are many different types of crude oils, not all crude oils perform the same way in a given refinery. As such, refineries are constantly trying to find the optimal crude oil for the products they aim to produce and for the operating conditions of the different units of the refinery. Conventionally, refineries attempt to optimize their crude oil slate using essentially trial and error methods. More specifically, refineries typically select their crude oil slate using a variety of factors including worldwide supply and demand (availability and price), refinery capability and configuration, transportation costs, and refining costs. After selecting the crude oil slate, refineries then evaluate the cost effectiveness of that crude oil slate on their processing units. Further, due to market conditions, refineries do not always received the same crude oil. As such, the impact of the crude oil slate on the processing units combined with the market conditions force refineries to frequently reevaluate their crude oil slate. Because current methods do not allow the refineries to predict the effect that a particular crude oil will have on its processing units, refineries continue to use trial and error methods to best determine the optimal crude oil for their processing units.

As such, there is a need for a way to predict the impact of a particular crude oil composition (e.g., a crude oil blend) on processing units to allow for more efficient crude oil slate optimization and to allow the selection of optimal operating conditions for a given crude oil slate.

SUMMARY

The present application is directed to a method for selecting optimal operating conditions for the hydrodesulfurization of a first liquid hydrocarbon feed in a reactor. The reactor has a reactor volume in the presence of a catalyst, such that it produces a product stream.

According to a first aspect, a method for selecting optimal operating conditions for the hydrodesulfurization of a first liquid hydrocarbon feed is provided in which a desired sulfur content of the product stream is selected. The method measures the carbazoles content of the first liquid hydrocarbon feed, calculates a reaction order for the first liquid hydrocarbon feed based on the measured carbazoles content, and calculates an operating severity index based on the calculated reaction order. The operating severity index comprises an operating temperature of the reactor to yield the product stream with the desired sulfur content.

According to another aspect, a method for selecting optimal operating conditions for the hydrodesulfurization of a liquid hydrocarbon feed is provided in which the carbazoles content of a plurality of liquid hydrocarbon feeds are measured to generate a database of the measured carbazoles content. The calculation of the reaction order can be done by determining a maximum carbazoles content in the database.

BRIEF DESCRIPTION OF THE DRAWING FIGURES

A more complete understanding of the invention and its many features and advantages will be attained by reference to the following detailed description and the accompanying drawings. It is important to note that the drawings illustrate only certain embodiments of the present invention and therefore should not be considered to limit its scope.

Figure 2:
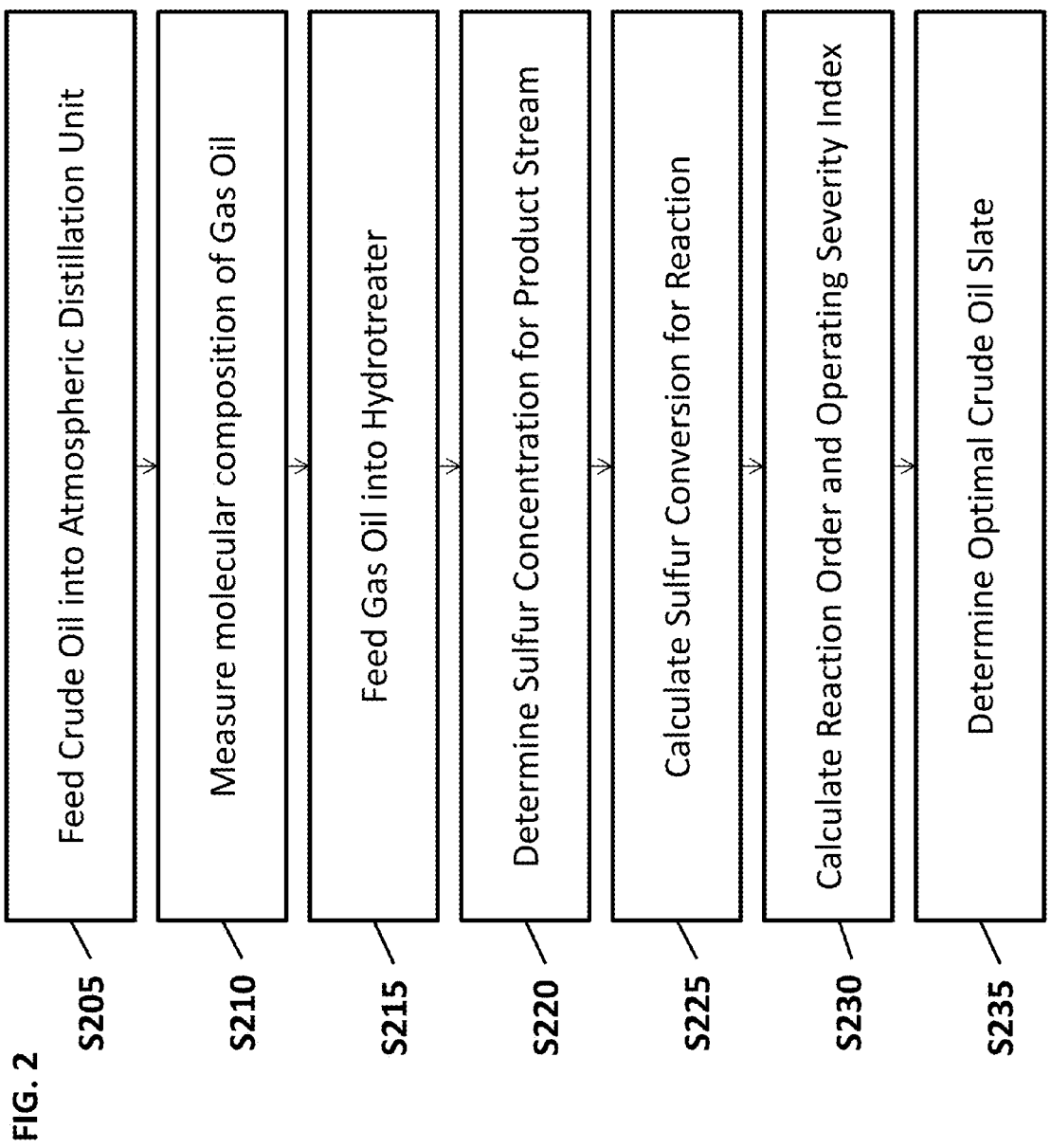
Figure 3:
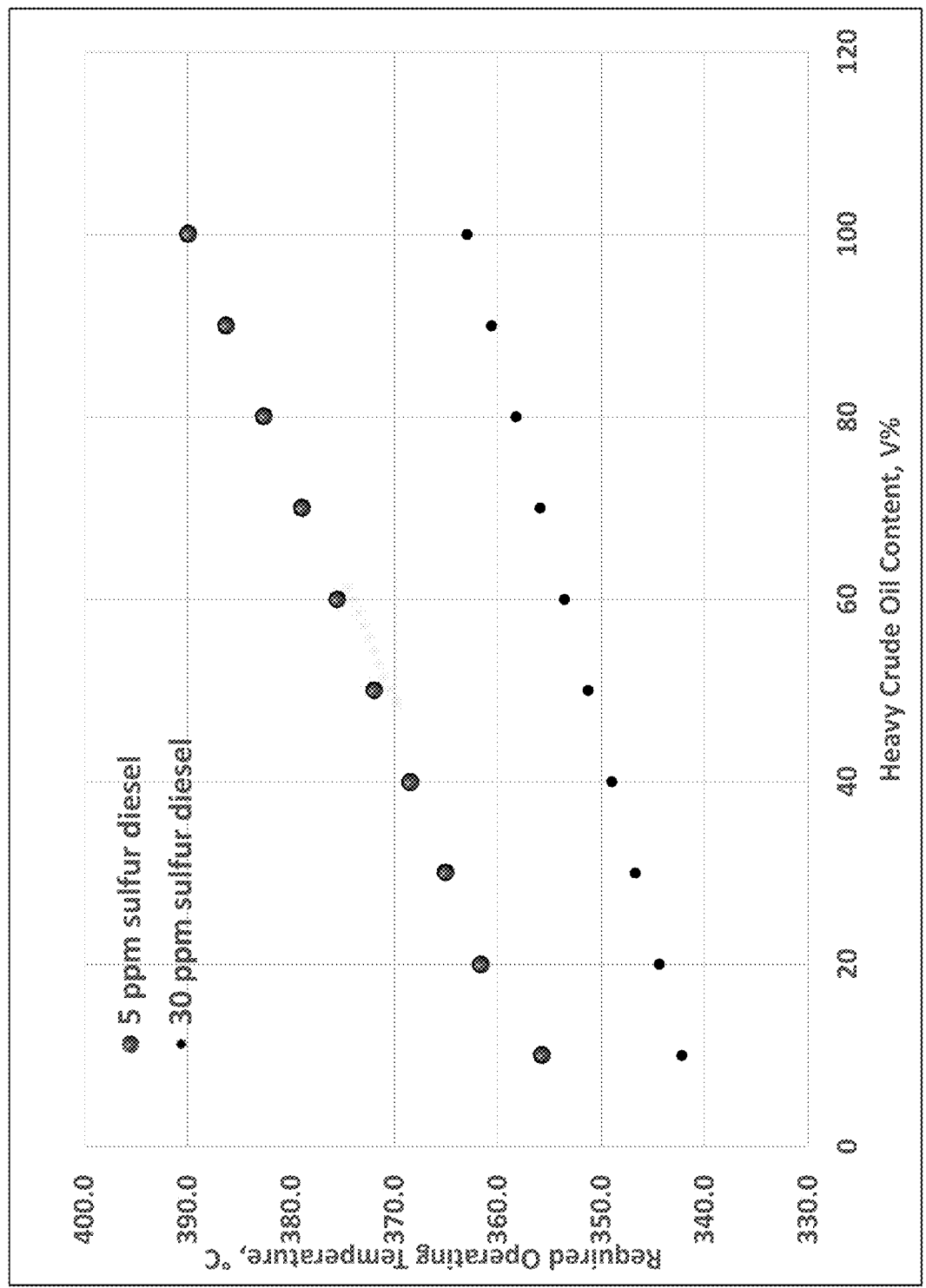

FIG. 1 shows a simplified schematic diagram of a portion of the refinery process, in accordance with at least one embodiment, including an atmospheric distillation unit and a hydrotreater;

FIG. 2 shows an exemplary process flow diagram of steps representing the method in accordance with at least one embodiment; and FIG. 3 shows an example graphical representation of the required operating temperature (° C.) for the processing of gas oil feedstocks with varying levels of light and heavy gas oil (0-100% heavy gas oil) in order to achieve either 5 ppm (Example 1) and 30 ppm (Example 2) levels of sulfur in the product stream, in accordance with at least one embodiment.

DETAILED DESCRIPTION OF CERTAIN EMBODIMENTS

As previously mentioned, conventional methods for determining the crude oil slate of a refinery rely on trial and error to a large extent.

These conventional methods, however, are not particular efficient as they require the refinery to continually reevaluate whether the crude oil slate should be changed based on the costs associated with using the current crude oil slate. Another problem with the conventional methods is that they do not consider the individual compositions of the gas oil streams or analyze the hydrocarbon fractions at the molecular level when determining the best crude oil slate for the refinery. Further, in conventional methods, bulk properties such as sulfur content, nitrogen content, and boiling point characteristics are measured, and then the crude oil fractions are tested in a pilot plant operation to determine processibility. This is a lengthy and costly method. As a result, achieving optimization can be a difficult task.

The methods of the present application are designed to overcome the deficiencies of the conventional methods for determining crude oil slate. As discussed in further detail below, the methods of the present application use molecular species and reactivity of the gas oil feeds to predict the process performance of other crude oils in a particular refinery unit. Thus, the methods of the present application allow a refinery to better select an advantageous crude oil slate for the particular refinery. In particular, the present method evaluates the gas oil streams based on their molecular characteristics (e.g., carbazoles content and hydrodesulfurization processability), which allows the refinery to calculate the performance of the hydrodesulfurization unit (e.g., diesel hydrotreating unit) and thereby adjust or optimize the crude oil slate to ensure the best performance of the diesel hydrotreating unit.

FIG. 1 shows a simplified flow diagram of a portion of the refinery process 100 in accordance with at least one embodiment. As shown, a crude oil stream 105 is first fed into an atmospheric distillation unit (ADU) 110, where it is distilled under atmospheric pressure to produce different fraction, including a gas oil stream(s) 115. The resulting gas oil stream 115 is then fed into a hydrodesulfurization unit 120 (e.g., a diesel hydrotreater) thereby producing a desired product stream 125 (e.g., diesel fuel). Hydrodesulfurization is a catalytic chemical process for removing sulfur from natural gas and from refined petroleum products, such as gasoline, diesel fuel, fuel oils, and the like. In an industrial hydrodesulfurization unit, such as in a refinery, the hydrodesulfurization reaction takes place in a fixed-bed reactor at elevated temperatures and elevated pressures, typically in the presence of a catalyst.

In the methods of the present application, the molecular characteristics of the gas oil stream 115 (resulting from the distillation of the current crude oil slate) are measured to determine the properties (e.g., concentrations of certain components) of the gas oil stream, such as carbazoles content and sulfur content. The gas oil stream 115 is then fed into a hydrotreater 120 to produce a product stream (e.g., diesel fuel), and the sulfur content of the product stream is then measured. In accordance with the one or more embodiments, the measurements of the gas oil and the diesel fuel are then used to determine the optimal crude oil slate for the refinery and/or the optimal operating conditions (e.g., temperature) for the diesel hydrotreating unit.

FIG. 2 shows a flow diagram of steps representing one exemplary method 200 in accordance with one or more embodiments. In step S205, the crude oil stream is first fed into the ADU 110, thereby producing a gas oil stream (the "first gas oil stream"). The resulting gas oil stream can have a boiling range from approximately 150° C. to approximately 400° C. In alternative embodiments, different types of feed streams can be fed into the ADU 110, including but not limited to, intermediate refinery distillate streams, such as those from cokers, fluid catalytic cracking, residue hydroconversion, or other nonconventional process streams, or a combination thereof. As mentioned herein, the ADU 110 serves to distill the crude oil into fractions.

In step S210, the molecular composition of the resulting gas oil stream is then measured. For example, in one or more implementations, the carbazole content of the gas oil stream is determined. A typical carbazole molecule is shown below.

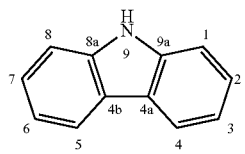 [SMILES: c1ccc2c(c1)[nH]c1ccccc12]

As defined herein, carbazoles are a group of aromatic heterocyclic nitrogen compounds, which includes acridines. More specifically, the carbazoles measured in the method of the present application is a group of carbazole compounds "lumped" together with basic nitrogen compounds such as acridine and its alkyl substituted derivatives. An acridine molecule structure is shown below.

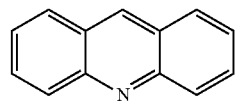 [SMILES: c1ccc2nc3ccccc3cc2c1]

The carbazole content of the gas oil stream can range from approximately 1 ppm to approximately 4,000 ppm.

The composition of the gas oil stream can also be measured to determine the concentration of other components of the gas oil including, but not limited to sulfur and nitrogen. In one or more embodiments, the sulfur content of the gas oil stream can range from approximately 10 ppm to approximately 40,000 ppm, whereas the nitrogen content of the gas oil stream can range from approximately 10 ppm to approximately 4,000 ppm. In at least one implementation, other properties of the gas oil stream can also be measured such as aromatic content and cetane number. The aromatic content of the gas oil can range from approximately 0.1% W to approximately 80% W.

The measurement of certain selected components of the gas oil stream, in particular the carbazoles content, nitrogen content, and sulfur content, can be accomplished using conventional standard methods such as ASTM D5453 for total sulfur or ASTM D4629 for total nitrogen or any number of spectroscopy and/or chromatography methods known in the art, including but not limited to fourier transform near-infrared spectroscopy, fourier transform infrared spectroscopy, fourier transform ion cyclotron mass spectroscopy, time of flight mass spectroscopy, ultraviolet visible spectroscopy, laser induced ultraviolet spectroscopy, nuclear magnetic spectroscopy, fluorescence spectroscopy, gas chromatography, high performance liquid chromatography, supercritical fluid chromatography, and single and two dimensional gas chromatography with specific sulfur and nitrogen detectors for sulfur and nitrogen species.

Continuing with FIG. 2, in step S215, the gas oil stream is fed into the hydrotreater 120, thereby producing the product stream (i.e., diesel fuel). The hydrotreater 120 can utilize any number of suitable catalysts, which are known by those having ordinary skill in the art. For example, the catalyst can be comprised of Co and/or Ni and/or Mo as active phase, and on a support comprised of alumina, silica, titania, zirconia, or zeolites or any combination thereof. In one or more embodiments, the catalyst can include at least one Group 8 metal and at least one Group 6 metal. In at least one embodiment, the amount of Group 8 metal in the catalyst ranges from approximately 1% wt. to approximately 30% wt., and the amount of Group 6 metal in the catalyst ranges from approximately 1% wt. to approximately 30% wt. based on the total weight of the catalyst.

In step S220 the sulfur concentration of the product stream (first product stream) is determined. The sulfur concentration can be determined by use of any one of the conventional standard and/or spectroscopy and/or chromatography method as listed above, or other suitable methods as are known in the art. As a result of the hydrotreating process, the product stream contains a desired sulfur content (i.e., a preselected sulfur content amount).

In step S225, after determining the sulfur concentration in the product stream, the sulfur content of the gas oil and the product stream are then used to determine the amount of sulfur converted (degree of hydrodesulfurization) using the following equation (measured by W %):

$$\text{Conversion}_{Sulfur} = \left(\frac{S_{Feed} - S_{Product}}{S_{Feed}}\right) \times 100$$

This equation is used to determine the performance of the hydrotreater unit, and to perform follow-up calculations to monitor the unit.

The operating conditions (e.g., temperature), of the hydrotreater 120 used to produce the product (first product stream) are known, and as disclosed herein, this information is used to calculate the optimal operating conditions for the hydrotreater 120 for a different feed to yield a product stream with the same preselected sulfur content. In other words, the product streams obtained from the two different feeds (e.g., gas oil streams) that are introduced into the hydrotreater unit 120 have the same sulfur content as a result of the operating conditions for the second feed being optimized in accordance with one or more methods of the present application.

Accordingly, in step S230, composition measurements of the gas oil (e.g., carbazoles content, sulfur content, and nitrogen content) and the product stream (e.g., sulfur content), and model parameters are used to determine the operation conditions for the next feedstock blend to be processed. More specifically, the gas oil stream obtained from a second type of crude oil that is distilled ("second gas oil") is measured to determine its composition, and in particular, to determine its carbazoles content and sulfur content. The carbazoles content of the second gas oil stream is then used to determine the reaction order for the second gas oil stream being processed using the following equation:

$$n = 1 + \frac{N_{carbazoles}}{N_{carbazoles-max}},$$

where $N_{carbazoles}$ equals the carbazoles content of the second gas oil, and $N_{carbazoles-max}$ equals the highest carbazoles content of any of the available gas oil streams in the database. More specifically, the $N_{carbazoles-max}$ value can be selected from the database, which includes the measured carbazoles content for gas oil streams that have been distilled from various different crude oils. For example, each crude oil (e.g., 100% light or 100% heavy or 50% light and 50% heavy, or other crude oils from other fields) that is initially distilled produces a gas oil stream that has a certain carbazoles content which can be measured as discussed herein.

Referring to the equation above, the reaction order ("n") equals 1 plus the carbazoles content of the second gas oil stream divided by the maximum carbazoles content of the available gas oil streams in the database. In one or more embodiments, the minimum reaction order is set to 1 and the maximum reaction order is set to 2. In other words, the minimum carbazole containing diesel oil has the reaction order of 1 and the maximum carbazole containing diesel oil has the reaction order of 2. As such, in one or more embodiments, the reaction orders are not true reaction orders, but rather a relative value that reflects the reactivity of the diesel oils relative to one another.

Once the reaction order is calculated, the rate constant (k) is determined using nth order rate equation as follows:
Nth Order Rate Constant $$1.\ k = LHSV * \left[\frac{S_{Product}^{(1-n)} - S_{Feed}^{(1-n)}}{n-1}\right].$$

The nth order rate constant is also a function of temperature, hydrogen partial pressure and catalyst age. In equation 2 (below), the temperature dependence is shown to follow the Arrhenius equation, where the hydrogen partial pressure dependency is exponential, and the catalyst age effect is linear.

$$2.\ k = A * \exp\left(\frac{-E_a}{R * T}\right) * HPP^b * (Catage * c).$$

The first equation is used to calculate the nth order reaction rate constant (k). In this equation, LHSV is the liquid hourly space velocity, and "n" equals the reaction order of the gas oil calculated in the previous equation. $S_{Feed}$ and $S_{Product}$ are the sulfur contents of the gas oil and the product stream, respectively. For a given sulfur level in the product, the sulfur conversions are calculated for gas oils to be processed. Then nth order rate constants are calculated from equation 1. The required operating temperature for the targeted sulfur level in the products is calculated from equation 2. Specifically, in equation 2, the process operating conditions (e.g., hydrogen partial pressure [HPP], catalyst age [catage]), model parameters (e.g., frequency factor [A], activation energy [$E_a$], hydrogen partial pressure dependency factor [b], catalyst deactivation factor [c], which are determined earlier and are available in the database), and the universal rate constant (R) are used to determine the operating severity index (operating temperature). The frequency factor, activation energy, and hydrogen partial pressure dependency factor can be calculated previously using available operating data for at least three temperature levels, hydrogen partial pressures, and multiple catalyst ages using equation 2.

Once the required operating temperature for the target sulfur level is determined for the second feed, the operating temperature of the hydrotreater reactor can be adjusted from the first operating temperature (operating temperature for the first feed) to the second operating temperature (operating temperature for the second feed) prior to delivery of the second liquid hydrocarbon feed (second gas oil) to the reactor. After delivery of the second feed to the hydrotreater reaction, which is operating at the operating temperature for the second feed, the reactor produces a second product stream. The second product stream has at least substantially the same sulfur content as the preselected first sulfur content (the sulfur content of the first product stream).

Based on the required operating temperature, which is the severity index for the operation, the optimal crude oil slate is then determined in step S235 for a given set of operating conditions. The resulting crude oil slate is "optimal" as it relates to the specific operating severity index (e.g., temperature) and the specific sulfur content of the product stream that is desired and preselected. More specifically, for a two crude oil system, using linear interpolation for the operating severity index of the first gas oil and the second gas oil and the percentage of heavy and light crude oil in the crude oil slate, the optimal crude oil slate can be determined for a particular operating severity index. Alternatively, the optimal operating severity index (operating temperature) for a particular crude oil slate can be determined using the same linear interpolation.

It should be understood that the methods of the present application are not limited to a two crude oil system (two gas oils). For example, in one or more implementations, the second crude oil (and resulting second gas oil) can later be used as a reference to determine the optimal operating conditions for a subsequent gas oil (e.g., a third gas oil), using the method discussed above, and so on.

It will be appreciated that the method of the present invention provides a means for calculating the optimal operating conditions (e.g. temperature) for a hydrotreater (hydrodesulfurization unit) based on the measured properties of the material to be introduced into the hydrotreater. In particular, the present method allows the optimal temperature of the hydrotreater to be selected based on the measured carbazoles content of the feed (gas oil stream) that is to be fed into the hydrotreater, whereby the product stream with preselected sulfur content is obtained.

In an embodiment in which the hydrotreating unit is a fixed-bed hydrotreating unit, the operating temperature changes with decreased catalytic activity. More specifically, the catalyst deactivates during the hydrotreating run and the activity loss is compensated by changing the operating temperature of the hydrotreating unit. For example, a unit may be designed to operate at 350° C. at the start of the run, and then the temperature is increased with catalyst deactivation during the run. When the end of run temperature is reached, the catalyst is fully deactivated and can then be replaced. Because the catalyst activity is a function of feedstock (gas oil) processed, the feedstock selection is made based on the operating temperature.

A more complete understanding of the method and its many features and advantages will be attained by reference to the following examples.

Example 1

A refinery feeds 100 V % light crude oil into the atmospheric distillation unit (ADU) to produce gas oil. The crude oil capacity of the ADU was 100,000 BPSD. The gas oil fraction boils in the range of 180-370° C. The molecular composition of the gas oil was determined. These measurements are shown in Table 1.

TABLE 1

Molecular Composition of Gas Oil
(100 V % Light Crude Oil)

| Constituents | Value |
| --- | --- |
| Sulfur | 8901 ppmw |
| Nitrogen | 49 ppmw |
| Carbazoles | 45 ppmw |

The gas oil was then fed into the hydrotreater and the gas oil feed rate was 39,200 BPSD. The hydrotreater yielded a diesel fuel fraction with a sulfur concentration of 5 ppm. The operating conditions for the hydrotreater are shown in Table 2.

TABLE 2

Hydrotreating Process Operating Conditions
(100 V % Light Crude Oil)

| Variable | Value |
| --- | --- |
| LHSV | 1.5 |
| Catalyst age | 512 hours |
| Hydrogen Partial Pressure | 26.5 bar |
| Temperature | 355° C. |

Due to outside circumstances, the refinery must change its crude oil slate, and the target crude oil slate is 50 V % heavy crude oil/50 V % light crude oil. As such, the following calculation must be performed in order to determine what would be the optimal operating conditions of the hydrotreater for gas oil from the target crude oil slate. Alternatively, if there is a limitation in the temperature of the hydrotreating unit (e.g., if the end of run temperature is reached), the optimal crude oil slate for that particular operating temperature can be determined using this calculation.

To do the calculation, 100 V % heavy crude oil is first fed into an ADU in laboratory scale unit, and its molecular composition is determined. If the crude oil to be processed is available in the database, the molecular composition of the gas oil is taken from the database without carrying-out laboratory distillation. These measurements are shown in Table 3.

TABLE 3

Molecular Composition of Gas Oil
(100 V % Heavy Crude Oil)

| Constituents | Value |
| --- | --- |
| Sulfur | 10061 ppmw |
| Nitrogen | 179 ppmw |
| Carbazoles | 96.5 ppmw |

Using the sulfur content of the gas oil streams to be processed and the sulfur content of the subsequent diesel fraction from the hydrotreater, the amount of sulfur converted ("hydrodesulfurization") by W % is determined using the following equation:

$$\text{Conversion}_{Sulfur} = \left(\frac{S_{Feed} - S_{Product}}{S_{Feed}}\right) \times 100$$

$\text{Conversion}_{Sulfur} = (10061 \text{ ppmw} - 5 \text{ ppmw}/10061) \times 100$ $\text{Conversion}_{Sulfur} = 99.95 \text{ W \%}$ Next, the target operations are calculated from 100 V % heavy crude oil models. More specifically, reaction order for the gas oil of the 100 V % heavy crude oil is determined using the following equation:

$$\text{Reaction\_order} = 1 + \frac{N_{carbazoles}}{N_{carbazoles-max}}$$

The carbazoles content of the gas oil of the 100 V % heavy crude oil is 96.5 ppmw, and the highest carbazoles content of any of the available gas oils is 167.4 ppmw. As such, the reaction order is calculated as follows:

Reaction order=1+(96.5 ppmw/167.4 ppmw)→Reaction order=1.576

Using the calculated reaction order, the nth order rate constant (k) is determined using the following equation:

$$k = LHSV * \left[\frac{S_{Product}^{(1-n)} - S_{feed}^{(1-n)}}{n-1}\right]$$

$k=1.5*[(5^{\wedge}(1-1.576))-(10061^{\wedge}(1-1.576))/(1.576-1)]$ $k=1.5*[0.387/0.576]$ $k=1.008$ The calculated rate constant (k) is then used in a modified Arrhenius equation (see below) along with the hydrotreating process operating conditions for the 100 V % light crude oil and model parameters, to determine the operating severity index, which in this example is the temperature. The model parameters are shown below in Table 4.

TABLE 4

Model Parameters for Hydrotreater

| Parameter | Value |
|---|---|
| Frequency factor (A) | 10357741002 |
| Hydrogen Partial Pressure dependency (b) | 1.155 |
| Activation energy ($E_a$) | 35,341 cal/mol |
| Catalyst deactivation factor (c) | 0.00001 |
| Universal gas constant (R) | 1.987 cal $K^{-1}$ $mol^{-1}$ |

Using the model parameters for the hydrotreater and the nth order rate constant (k) calculated for 100 V % heavy crude oil, the operating severity index (temperature) for 100 V % heavy crude oil is calculated.

$$k = A * \exp\left(\frac{-E_a}{R*T}\right) * HPP^b * (Cat_{age} * c)$$

$1.008=10357741002*e^{\wedge}(-35,341/1.987*T)$
$\quad *26.5^{\wedge}1.155*(512*0.00001)$ $1.008=4.57391E11*e^{\wedge}(-35,341/1.987*T)$ $2.2038E-12=e^{\wedge}(-35,341/1.987*T)$ $\ln(2.2038E-12)=\ln(e^{\wedge}(-35,341/1.987*T))$ $-26.8408=-35,341/1.987*T$ $-26.8408=-17,786.1097/T$ $663K=T$ $390°\ C.=T$ The operating severity index (temperature) for 100 V % heavy crude oil and 100 V % light crude oil can then be used to determine the optimal operating severity index for other crude oil blends for the refinery using linear interpolations, as shown in FIG. 3 and Table 5 below.

TABLE 5

Operating Temperature Requirement for Hydrotreater as a Function of Heavy Crude Oil Content

| Crude Oil Ratio | | Targeted Sulfur in the hydrotreated diesel 5 ppm | |
|---|---|---|---|
| Heavy Crude Oil | Light Crude Oil | | |
| % | % | ΔT | ROT |
| 0 | 100 | 0.0 | 355.0 |
| 10 | 90 | 3.0 | 355.8 |
| 20 | 80 | 6.7 | 361.7 |
| 30 | 70 | 10.1 | 365.1 |
| 40 | 60 | 13.5 | 368.5 |
| 50 | 50 | 17.0 | 372.0 |
| 60 | 40 | 20.5 | 375.5 |
| 70 | 30 | 24.1 | 379.0 |
| 80 | 20 | 27.7 | 382.7 |
| 90 | 10 | 31.3 | 386.3 |
| 100 | 0 | 35.0 | 390.0 |

ΔT = change in temperature (° C.);
ROT = required operating temperature (° C.).

Based on these linear interpolations, the optimal operating temperature for the hydrotreater when using the target crude oil slate (50 V % heavy crude oil/50 V % light crude oil) is 372° C. Thus, in order for the hydrotreater to obtain 5 ppmw diesel fraction from the same hydrotreater unit, but using the gas oil from the target crude oil slate, the operating temperature must be increased by 17° C. as compared with the original operating temperature (355° C.).

In an instance in which the refinery does not have a target crude oil slate, but wants to determine the optimal crude oil slate based on the operating severity index (e.g., temperature) of the hydrotreater unit, the above linear interpolation can still be used to determine what is the optimal crude oil slates for the particular operating temperature.

Example 2

A refinery feeds 100 V % light crude oil into the atmospheric distillation unit (ADU) to produce gas oil. The crude oil capacity of the ADU was 100,000 BPSD. The gas oil fraction boils in the range of 180-370° C. The molecular composition of the gas oil was determined. These measurements are shown in Table 6.

TABLE 6

Molecular Composition of Gas Oil (100 V % Light Crude Oil)

| Constituents | Value |
|---|---|
| Sulfur | 8901 ppmw |
| Nitrogen | 49 ppmw |
| Carbazoles | 45 ppmw |

The gas oil was then fed into the hydrotreater and the gas oil feed rate was 39,200 BPSD. The hydrotreater yielded a diesel fuel fraction with a sulfur concentration of 30 ppm. The operating conditions for the hydrotreater are shown in Table 7.

TABLE 7

Hydrotreating Process Operating Conditions
(100 V % Light Crude Oil)

| Variable | Value |
|---|---|
| LHSV | 1.5 |
| Catalyst age | 512 hours |
| Hydrogen Partial Pressure | 26.5 bar |
| Temperature | 340° C. |

Due to outside circumstances, the refinery must change its crude oil slate, and the target crude oil slate is 50 V % heavy crude oil/50 V % light crude oil. As such, the following calculation must be performed in order to determine what would be the optimal operating conditions of the hydrotreater for gas oil from the target crude oil slate. Alternatively, if there is a limitation in the temperature of the hydrotreating unit (e.g., if the end of run temperature is reached), the optimal crude oil slate for that particular operating temperature can be determined using this calculation. To do the calculation, 100 V % heavy crude oil is first fed into an ADU, and its molecular composition is determined. These measurements are shown in Table 8.

TABLE 8

Molecular Composition of Gas Oil
(100 V % Heavy Crude Oil)

| Constituents | Value |
|---|---|
| Sulfur | 10061 ppmw |
| Nitrogen | 179 ppmw |
| Carbazoles | 96.5 ppmw |

Using the sulfur content of the gas oil streams from the 100 V % light crude oil and the sulfur content of the subsequent diesel fraction from the hydrotreater, the amount of sulfur converted ("hydrodesulfurization") by W % is determined using the following equation:

$$\text{Conversion}_{Sulfur} = \left(\frac{S_{Feed} - S_{Product}}{S_{Feed}}\right) \times 100$$

$$\text{Conversion}_{Sulfur} = (10061 \text{ ppmw} - 30 \text{ ppmw}/10061) \times 100$$

$$\text{Conversion}_{Sulfur} = 99.7 \text{ W \%}$$

Next, the target operations are calculated from 100 V % heavy crude oil models. More specifically, reaction order for the gas oil of the 100 V % heavy crude oil is determined using the following equation:

$$\text{Reaction\_order} = 1 + \frac{N_{carbazoles}}{N_{carbazoles-max}}$$

The carbazoles content of the gas oil of the 100 V % heavy crude oil is 96.5 ppmw, and the highest carbazoles content of any of the available gas oils is 167.4 ppmw. As such, the reaction order is calculated as follows:

Reaction order=1+(96.5 ppmw/167.4 ppmw)

Reaction order=1.576

Using the calculated reaction order, the nth order rate constant (k) is determined using the following equation:

$$k = LHSV * \left[\frac{S_{Product}^{(1-n)} - S_{Feed}^{(1-n)}}{n-1}\right]$$

$k=1.5*[(30\char`\^(1-1.576))-(10061\char`\^(1-1.576))/(1.576-1)]$ $k=1.5*[0.1360/0.576]$ $k=0.354$ The calculated rate constant (k) is then used in a modified Arrhenius equation (see below) along with the hydrotreating process operating conditions for the 100 V % light crude oil and model parameters, to determine the operating severity index, which in this example is the temperature. The model parameters are shown below in Table 9.

TABLE 9

Model Parameters for Hydrotreater

| Parameter | Value |
|---|---|
| Frequency factor (A) | 10357741002 |
| Hydrogen Partial Pressure dependency (b) | 1.155 |
| Activation energy ($E_a$) | 35,341 cal/mol |
| Catalyst deactivation factor (c) | 0.00001 |
| Universal gas constant (R) | 1.987 cal K$^{-1}$ mol$^{-1}$ |

Using the model parameters for the hydrotreater and the nth order rate constant (k) calculated for 100 V % heavy crude oil, the operating severity index (temperature) for 100 V % heavy crude oil is calculated.

$$k = A * \exp\left(\frac{-E_a}{R*T}\right) * HPP^b * (Cat_{age} * c)$$

$0.354=10357741002*e\char`\^(-35,341/1.987*T)*26.5\char`\^1.155*(512*0.00001)$ $0.354=4.57391E11*e\char`\^(-35,341/1.987*T)$ $7.7395E-13=e\char`\^(-35,341/1.987*T)$ $\ln(7.7395E-13)=\ln(e\char`\^(-35,341/1.987*T))$ $-27.8872=-35,341/1.987*T$ $-27.8872=-17,786.1097/T$ $638K=T$ $365° C.=T$ The operating severity index (temperature) for 100 V % heavy crude oil and 100 V % light crude oil can then be used to determine the optimal operating severity index for other crude oil blends for the refinery using linear interpolations, as shown in FIG. 3 and Table 10 below.

TABLE 10

Operating Temperature Requirement for Hydrotreater as a Function of Heavy Crude Oil Content

| Crude Oil Ratio | | Targeted Sulfur in the hydrotreated diesel 30 ppm | |
|---|---|---|---|
| Heavy Crude Oil | Light Crude Oil | | |
| % | % | ΔT | ROT |
| 0 | 100 | 0.0 | 340.0 |
| 10 | 90 | 2.2 | 342.2 |
| 20 | 80 | 4.5 | 344.4 |
| 30 | 70 | 6.7 | 346.7 |
| 40 | 60 | 5.0 | 349.0 |
| 50 | 50 | 11.3 | 351.3 |
| 60 | 40 | 13.6 | 353.6 |
| 70 | 30 | 15.9 | 355.9 |
| 80 | 20 | 18.3 | 358.3 |
| 90 | 10 | 20.6 | 360.6 |
| 100 | 0 | 23.0 | 363.0 |

Based on these linear interpolations, the optimal operating temperature for the hydrotreater when using the target crude oil slate (50 V % heavy crude oil/50 V % light crude oil) is 351.3° C. Thus, in order for the hydrotreater to obtain a 30 ppmw diesel fraction from the same hydrotreater unit, but using the gas oil from the target crude oil slate, the operating temperature must be increased by 11.3° C. as compared with the original operating temperature (340° C.).

While the present invention has been described above using specific embodiments and examples, there are many variations and modifications that will be apparent to those having ordinary skill in the art. As such, the described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A method for selecting optimal operating conditions for the hydrodesulfurization of a liquid hydrocarbon feed in a reactor having a reactor volume in the presence of a catalyst to produce a product stream comprising the steps of:
measuring a carbazoles content of a plurality of liquid hydrocarbon feeds that are produced from distilling a plurality of initial liquid hydrocarbon feeds;
generating a database of the plurality of liquid hydrocarbon feeds comprising their respective measured carbazoles contents;
selecting a first liquid hydrocarbon feed for introduction into the reactor, wherein the first liquid hydrocarbon feed is selected from the generated database;
selecting a desired sulfur content of a first product stream produced in the reactor from the first liquid hydrocarbon feed;
calculating a reaction order for the first liquid hydrocarbon feed based on the measured carbazoles content of the first liquid hydrocarbon, wherein the step of calculating the reaction order comprises the step of determining a highest measured carbazoles content in the database and the reaction order of the first liquid hydrocarbon feed is calculated using the following equation:

$$n = 1 + \frac{N_{carbazoles}}{N_{carbazoles-max}},$$

where n is the reaction order, $N_{carbazoles}$ equals the carbazoles content of the first liquid hydrocarbon feed, and $N_{carbazoles-max}$ equals the highest measured carbazoles content in the database; and
calculating an operating severity index based on the calculated reaction order, wherein the operating severity index comprises an operating temperature of the reactor to yield the first product stream with the desired sulfur content from the first liquid hydrocarbon feed, wherein the operating severity index is calculated using the following equations:

$$k = LHSV * \left[ \frac{S_{Product}^{(1-n)} - S_{Feed}^{(1-n)}}{n-1} \right]. \quad 1$$

$$k = A * \exp\left(\frac{-E_a}{R*T}\right) * HPP^b * (Catage*c). \quad 2$$

wherein LHSV is a liquid hourly space velocity, and n equals the reaction order of the first liquid hydrocarbon feed, $S_{Feed}$ equals sulfur content of the first liquid hydrocarbon feed; $S_{Product}$ comprises the desired sulfur content of the first product stream; k is the nth order reaction rate constant, HPP is the hydrogen partial pressure, Catage is the catalyst age, A is the frequency factor, [$E_a$] is the activation energy, b is the hydrogen partial pressure dependency factor, c is the catalyst deactivation factor, R is the universal rate constant (R) and T is the temperature of the reactor.

2. The method of claim 1, wherein the first liquid hydrocarbon feed and the plurality of liquid hydrocarbon feeds both comprise gas oil streams produced from distillation of crude oils.

3. The method of claim 1, wherein the reactor comprises a diesel hydrotreater, the first liquid hydrocarbon feed comprises a gas oil stream and the product stream comprises diesel fuel.

4. The method of claim 1, wherein the first liquid hydrocarbon stream is produced from at least one of crude oils, intermediate refinery distillate streams or a combination thereof.

5. The method of claim 1, wherein the catalyst comprises at least one Group 8 metal and at least one Group 6 metal.

6. The method of claim 5, wherein the amount of the Group 8 metal is from about 1 to about 30 wt. % and the amount of the Group 6 metal is from about 1 to about 30 wt. % based on the total weight of the catalyst.

7. The method of claim 1, wherein the first liquid hydrocarbon feed has a boiling range of about 150° C. to about 400 C.

8. The method of claim 1, wherein the first liquid hydrocarbon feed contains sulfur from about 10 ppm to about 40,000 ppm.

9. The method of claim 1, wherein the first liquid hydrocarbon feed has carbazoles content from about 1 ppm to about 4,000 ppm.

10. The method of claim 1, wherein the first liquid hydrocarbon feed contains aromatics from about 0.1 wt. % to about 80 wt. % based on a total weight of the first liquid hydrocarbon feed.

11. The method of claim 1, further comprising the steps of:
selecting a second liquid hydrocarbon feed for introduction into the reactor to form a second product stream having at least substantially the same selected sulfur content as the first product stream, measuring a carbazoles content of the second liquid hydrocarbon feed;

calculating a reaction order for the second liquid hydrocarbon feed based on the measured carbazoles content of the second liquid hydrocarbon feed; and calculating an operating severity index of the second liquid hydrocarbon feed based on the selected sulfur content of the second product stream, wherein the operating severity index comprises an operating temperature of the reactor to yield the second product stream with the desired sulfur content from the second liquid hydrocarbon feed.

12. A method for operating a hydrodesulfurization unit at optimal operating conditions for the hydrodesulfurization of a liquid hydrocarbon feed in a reactor of the hydrodesulfurization unit, the reactor having a reactor volume in the presence of a catalyst to produce a product stream, comprising the steps of:

measuring a carbazoles content of a plurality of liquid hydrocarbon feeds that are produced from distilling a plurality of initial liquid hydrocarbon feeds;

generating a database of the plurality of liquid hydrocarbon feeds comprising their respective measured carbazoles contents;

selecting a first liquid hydrocarbon feed for introduction into the reactor which is operating under a first set of operating conditions including a first operating temperature to yield a pre-selected first sulfur content of a first product stream produced from the first liquid hydrocarbon feed, wherein the first liquid hydrocarbon feed is selected from the generated database;

selecting a second liquid hydrocarbon feed for introduction into the reactor to form a second product stream having at least substantially the same pre-selected first sulfur content;

measuring a carbazoles content and a sulfur content of the second liquid hydrocarbon feed;

calculating a reaction order for the second liquid hydrocarbon feed based on the measured carbazoles content of the second liquid hydrocarbon feed, wherein the step of calculating the reaction order comprises the step of determining a highest measured carbazoles content in the database and the reaction order of the second liquid hydrocarbon feed is calculated using the following equation:

$$n = 1 + \frac{N_{carbazoles}}{N_{carbazoles-max}},$$

where n is the reaction order, $N_{carbazoles}$ equals the carbazoles content of the second liquid hydrocarbon feed, and $N_{carbazoles-max}$ equals the highest measured carbazoles content in the database; and calculating an operating severity index of the second liquid hydrocarbon feed based on the selected sulfur content of the product stream, wherein the operating severity index comprises a second operating temperature of the reactor to yield the second product stream having at least substantially the pre-selected first sulfur content, wherein the operating severity index is calculated using the following equations:

$$k = LHSV * \left[ \frac{S_{Product}^{(1-n)} - S_{Feed}^{(1-n)}}{n-1} \right]. \quad 1$$

$$k = A * \exp\left(\frac{-E_a}{R*T}\right) * HPP^b * (Catage * c). \quad 2$$

wherein LHSV is a liquid hourly space velocity, and n equals the reaction order of the second liquid hydrocarbon feed, $S_{Feed}$ equals the sulfur content of the second liquid hydrocarbon feed; $S_{Product}$ comprises the pre-selected first sulfur content of the first product stream; k is the nth order reaction rate constant, HPP is the hydrogen partial pressure, Catage is the catalyst age, A is the frequency factor, $[E_a]$ is the activation energy, b is the hydrogen partial pressure dependency factor, c is the catalyst deactivation factor, R is the universal rate constant (R) and T is the temperature of the reactor; and adjusting the operating temperature of the reactor from the first operating temperature to the second operating temperature prior to delivery of the second liquid hydrocarbon feed to the reactor.

13. The method of claim 12, wherein the first and second liquid hydrocarbon feeds and the plurality of liquid hydrocarbon feeds both comprise gas oil streams produced from distillation of crude oils.

14. The method of claim 12, wherein the reactor comprises a diesel hydrotreater, the first and second liquid hydrocarbon feeds comprise separate gas oil streams and the product stream comprises diesel fuel.

15. The method of claim 14, wherein the first and second liquid hydrocarbon streams are produced from at least one of crude oils, intermediate refinery distillate streams or a combination thereof.

16. The method of claim 12, wherein the catalyst comprises at least one Group 8 metal and at least one Group 6 metal.

17. The method of claim 16, wherein the amount of the Group 8 metal is from about 1 to about 30 wt. % and the amount of the Group 6 metal is from about 1 to about 30 wt. % based on the total weight of the catalyst.

18. The method of claim 12, wherein the first and second liquid hydrocarbon feeds have a boiling range of about 150° C. to about 400° C.

19. The method of claim 12, wherein the first and second liquid hydrocarbon feeds contain sulfur from about 10 ppm to about 40,000 ppm.

20. The method of claim 12, wherein the first and second liquid hydrocarbon feeds have carbazoles content from about 1 ppm to about 4,000 ppm.

21. The method of claim 12, wherein the first and second liquid hydrocarbon feeds contain aromatics from about 0.1 wt. % to about 80 wt. % based on a total weight of each respective liquid hydrocarbon feed.

* * * * *